United States Patent [19]

Cazarra et al.

[11] 4,344,815
[45] Aug. 17, 1982

[54] METHOD FOR CHARACTERIZING THE OXYGEN CONTENTS OF CZOCHRALSKI GROWN SILICON RODS

[75] Inventors: Victor Cazarra; André Schwab, both of Mennecy; Patrick Zunino, Evry, all of France

[73] Assignee: International Business Machines Corporation, Armonk, N.Y.

[21] Appl. No.: 158,003

[22] Filed: Jun. 9, 1980

[30] Foreign Application Priority Data

Jun. 29, 1979 [FR] France .................... 79 17302

[51] Int. Cl.$^3$ ............................................. C30B 15/00
[52] U.S. Cl. .............................. 156/601; 156/617 SP
[58] Field of Search ......... 156/601, 617 SP, DIG. 73, 156/DIG. 66; 252/181.1; 23/230 R; 148/1.5, 172

[56] References Cited

U.S. PATENT DOCUMENTS

3,725,148  4/1973  Kendall ............................. 148/186
4,140,570  2/1979  Voltmer et al. .................. 156/617
4,220,483  9/1980  Cazcarra .......................... 148/1.5

OTHER PUBLICATIONS

S. M. Hu et al., "Gettering by Oxygen Precipitation," IBM TDB, vol. 19, No. 12, May 1977, pp. 4618-4619.
F. W. Voltmer et al., "Anomalous Resistivity Profiles in Long Silicon Crystals Grown by the Czochralski Method", Journal of Crystal Growth, vol. 19, No. 3, 1973, pp. 215-217.
R. B. Herring, "Silicon Wafer Technology-State of the Art 1976," Solid State Technology, vol. 19, No. 5, May 1976, pp. 37-42, 54.
C. S. Fuller et al., "Interactions Between Oxygen and Acceptor Elements in Silicon," Journal of Applied Physics, vol. 29, No. 8, 1958, pp. 1264-1265.
G. Bemski et al., "Quenched-In Defects in p-Type Silicon," Journal of Applied Physics, vol. 35, No. 10, 1964, pp. 2983-2985.
Wouters et al., "The Electrical Conductivity of Silicon Between 500° C. and 1200° C.," Philips Research Reports, vol. 31, No. 3, 1976, pp. 278-283.
K. Yamamoto et al., "Lifetime Improvement in Czochralski-Grown Silicon Wafers by the Use of a Two-Step Annealing," Applied Physics Letters, vol. 36, No. 3, 1980, pp. 195-197.
A. Murgai et al., "Effect of Microscopic Growth Rate on Oxygen Microsegregation and Swirl Defect Distribution in Czochralski-Grown Silicon," Journal of the Electrochemical Society, vol. 126, No. 12, 1979, pp. 2240-2245.

*Primary Examiner*—Hiram Bernstein
*Attorney, Agent, or Firm*—Henry Powers

[57] ABSTRACT

The oxygen content of Czochralski grown silicon rods is characterized by annealing portions of the rods at selected times and temperatures and measuring the resistivity shift which is then related to the oxygen content of that portion of the rod. The rod can be selected for use in unipolar or bipolar device manufacture prior to cutting the rod into wafers.

12 Claims, 13 Drawing Figures

METHOD FOR CHARACTERIZING THE OXYGEN CONTENTS OF CZOCHRALSKI GROWN SILICON RODS

TECHNICAL FIELD

This invention relates to the manufacture of integrated circuits provided with semiconducting devices and more particularly, to a method for characterizing the oxygen contents of semiconductor rods and in particular, of Czochralski grown silicon rods.

The current tendency in microelectronics is for more dense integrated semiconductor circuit chips, which requires a better knowledge of the characteristics in the solid state physics domain, of the substrates in use. In general, the substrates in use are made of single crystal silicon obtained either by the Czochralski method or by the floating-zone method.

It is known that the Czochralski grown silicon rods (or CZ rods) have an oxygen content exceeding the oxygen content of the rods obtained by applying the so-called floating zone method (or FZ rods). In effect, this contamination is due to the reaction of liquid silicon on the walls of the silica crucible, which produces SiO. Therefore, a quantity of oxygen which cannot be neglected is introduced into silicon. The average oxygen content of the CZ rods is from 2 to $20 \times 10^{17}$ atoms per $cm^3$ of silicon while the FZ rods show an average oxygen content of from 0.01 to $0.2 \times 10^{17}$ atoms per $cm^3$ of silicon. The high oxygen concentration of the silicon has significant electrical consequences and affects the crystal purity. In effect, from the electrical point of view, the oxygen atoms have a tendency to diffuse when growing the rods and to aggregate to form successive aggregates of $SiO_2$, $SiO_3$, ..., $SiO_n$. Some of them act as donors and therefore, can very much affect the silicon conductivity and resistivity.

Resistivity is an essential parameter of the semiconductor material. From the resistivity, it is possible to determine the electrically active impurities. Resistivity will be measured by using the conventional so called "four points" method. The type of conductivity will be determined by using the conventional thermo electrical method. To show how the resistivity depends on the oxygen content, it is determined that the generation of $10^{14}$ donors per $cm^3$ in a P type wafer with a resistivity of 16 $\Omega.cm$ brings its resistivity to 18 $\Omega.cm$, and that the generation of $5.10^{14}$ donors per $cm^3$ brings said resistivity to 36 $\Omega.cm$ while the generation of $2.10^{15}$ donors per $cm^3$ transforms the P type material into N type material with a resistivity of 15 $\Omega.cm$. The reader is referred to the article of Irvin entitled "Resistivity of Bulk Silicon and of Diffused Layer" in the Bell System Techn. Journal, Vol. 41, pages 387-410, March 1962.

In addition, these agglomerates in the crystal structure can cause dislocations and various defects to appear and affect the crystal quality of the material and therefore, the reliability of the final product.

However, as long as the phenomenon is well controlled, it is generally admitted that the presence of oxygen in the silicon substrates is generally advantageous. Said agglomerates or precipitates will be used later for gettering undesired impurities when performing the various thermal cycles required for manufacturing integrated circuits. This problem is described in detail in French patent application No. 78 26223 filed on Sept. 8, 1978 by the applicant of the present invention which corresponds to U.S. application No. 066593 filed Aug. 14, 1979 now U.S. Pat. No. 4,220,483 granted Sept. 2, 1980.

In the present application, the contamination due to the carbon atoms is not taken into account, as a matter of fact the effect is probably less important then the effect of the oxygen atoms, but it cannot be neglected.

The interstitial oxygen concentration is generally measured by using an I.R. spectrometer from the absorption peak situated at a wavelength of 9 $\mu m$. Thus, a coefficient of absorption, $\alpha_{ox}$, which is proportional to the oxygen concentration is obtained. The proportionality constant will be defined from samples the oxygen level of which has been measured by using other methods (for instance, the activation analysis). In this case, this proportionality constant in accordance with U.S. standard ASTM, is of 0.63 ppmA/$cm^{-1}$. The ppmA unit (part per million atomic) corresponds to $0.5 \times 10^{17}$ atoms per $cm^3$ of silicon. In general, the IR method is accurate but care should be taken about the surface condition of the sample and sometimes corrections relating to the number of carriers, should be applied.

STATE OF THE ART

The silicon wafers cut from CZ rods contain oxygen. It is essential to know the behavior of said wafers when they are submitted to various thermal treatments (diffusion, oxidation, etc.) and in particular, to know why some noticeable changes appear in the resistivity or even in the type of conductivity. The effect of oxygen on the electrical properties of CZ silicon substrates has been experimentally studied by performing annealing operations at various temperatures.

Fuller et al. in Physical Review 96, 833(A) 1955, show that annealing operations performed within a temperature range of 400° to 500° C. considerably affect the resistivity of CZ rods.

Below 400° C., donor complex ions are generated but there is no noticeable maximum which can be detected even after an annealing operation of 500 hours as shown in the article of W. Kaiser et al., Phys. Rev. 112, 1546, 1958. Kaiser has also shown (Phys. Rev. 105, 1751, 1957) on the one hand, that an annealing operation performed at 450° C. for approximately 100 hours generates a maximum of donors and, on the other hand, the relation which exists between the initial oxygen concentration and the number of the complex donor ions.

It is also known that at about 650° C., even for a relatively short period of time (30 min.), these electrically active complex ions formed at 450° C. are destroyed and that the oxygen atoms precipitate into a new electrically inactive phase ($SiO_2$). That is why this temperature is always used for carrying out the socalled "stabilization anneal" which sets the resistivity of the CZ rods. A stabilization anneal can also be performed at 1000° C. for relatively long periods of time (20 hours) but this temperature is obviously less advantageous than the above indicated temperature of 650° C.

Nowadays, the method consists in cutting all the wafers from a CZ rod stabilized at 650° C. and rectifying them. Then, said wafers are lapped, polished and their oxygen level is measured by using IR techniques. At last, they are sorted one by one to only the wafers meeting the oxygen requirement. This method is very expensive and considerably restricts the throughput of the "material" production lines.

SUMMARY OF THE INVENTION

This specification describes a method for characterizing wafers according to the resistivity shift measured on portions of CZ rods which have been submitted to particular thermal treatments performed at a temperature in the range of approximately 600° to 900° C., for approximately 1 to 10 hours. Today, it is necessary to have silicon wafers the oxygen concentration of which is known, which precipitate oxygen more or less rapidly according to the devices to be fabricated and which must meet very tight resistivity requirements.

In a first application concerning bipolar devices, it is required to detect portions of rods in which the oxygen level is lower than approximately 35–36 ppmA. In another application concerning unipolar devices, it is required to detect portions of rods in which the oxygen level exceeds approximately 30 ppmA.

Therefore, an object of this invention is to provide a sensitive and accurate method for characterizing the oxygen contents of silicon rods to process only the portion with the desired oxygen concentration.

Another object of this invention is to enable the reader to forecast the maximum amount of oxygen atoms which can precipitate in certain wafers cut from CZ rods.

Another object of this invention is to provide the production lines with wafers cut from CZ rods showing a stable resistivity (or which varies only by a specified amount).

In a known manner, the resistivity of CZ rods is stabilized at a temperature close to 600° C. (between the two peaks of resistivity at 450° and 750° C., which will be pointed out later) and for 0.5 to 3 hours (which will avoid any generation of donors).

Then, the characterizing method of this invention comprises the following steps: cutting a portion of the rod which is approximately 1 cm thick from any end of the rod (depending whether one wants to have a maximum or a minimum oxygen content); measuring its resistivity; annealing this portion at a temperature ranging from 600° to 900° C. for a sufficient period of time in a neutral atmosphere ($N_2$); chemically etching the surface of said portion to clean it and measuring the resistivity increment. It is the measured value of this increment which will ultimately characterize the oxygen content of the rod. In practice, it will be seen later than the temperature ranges from 650° to 850° C. and the period of time, from 1 to 6 hours.

This method for carrying out an indirect measurement of the oxygen level will make the user able to determine quickly the portions of the CZ rods with the oxygen level required and, therefore, to cut, lap and polish only the wafers able to be sent to the production lines.

In a preferred embodiment ensuring a maximum oxygen concentration of 35–36 ppmA, the annealing temperature is 825° C., the annealing duration close to 2 hours and the resistivity increment of the portion cut from the head of the rod, null or very small. In effect, for a p type wafer with an initial resistivity around 19 Ω.cm, the generation of $10^{14}$ donors per cm$^3$ makes said resistivity vary by 3 Ω.cm (refer to the above indicated IRVIN works ), which shows the sensitivity of the method of this invention.

In addition, when it is desired to generate precipitates to increase gettering, it is possible, according to the above referenced French patent application No. 78 26233, to submit the rod to appropriate thermal treatments and to characterize the precipitation by using the method of this invention. However, if the wafers have been treated below 850° C., very strong generations of precipitates could be detected due to the variations of the resistivity. In general, these variations will be corrected when carrying out thermal treatments on the production lines.

The foregoing and other objects, features and advantages of the invention will be apparent from the following more particular description of a preferred embodiment of the invention, as illustrated in the accompanying drawings.

DISCLOSURE OF THE INVENTION

1. Generating donors including oxygen through thermal treatment.

Figure 1:
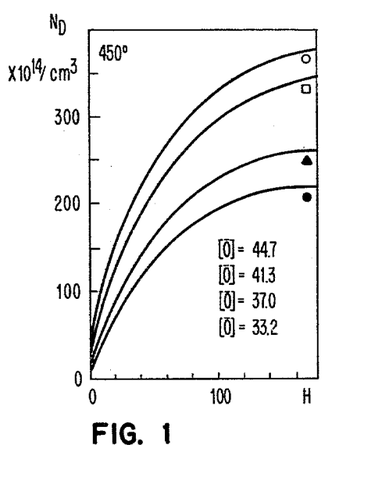
FIG. 1 shows the number of donors generated ($N_D$) in accordance with the duration of the annealing operation (t) in hours at 450° C. for various initial concentrations of oxygen $[\overline{O}]$.

(a) Around 450° C.: As indicated above, Fuller has set the problem for thermal treatments close to 450° C. In his article, Kaiser has provided explanatory theories based on the generation of donor complexes of the $SiO_4$ type at these temperatures around 450° C., which are destroyed at higher temperatured ($\simeq 600°$ C.). Said generation was proportional to the fourth power of the oxygen concentration $[O]^4$ and goes through a maximum, which is consistent with the experiments carried out. The results of FIG. 1 corroborates Kaiser's work. However, the information relating to the oxygen which can be obtained from the resistivity variations, is too inaccurate (see the high standard shifts plotted on FIG. 2) to be used on the production line.

Figure 3:
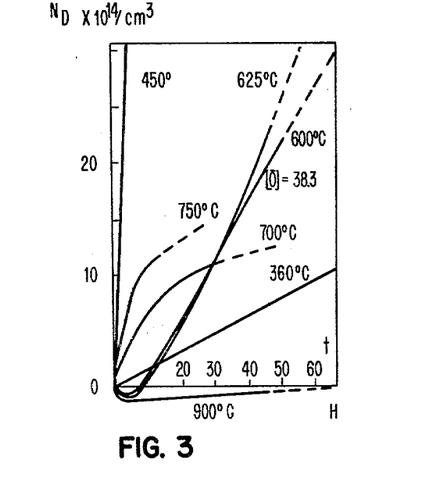
FIG. 3 shows the number of donors $N_D$ generated according to the duration t of the annealing operations given in hours, for various annealing temperatures and wafers with an initial concentration of oxygen $[\overline{O}]$ of 38.3 ppmA.

(b) At temperatures exceeding 450° C.: The curves plotted on FIG. 3 show that for wafers with a high oxygen level, donors are very quickly generated at temperatures close to 750° C. The results of systematic experiments performed at 600° C., 650° C., 750° C., 825° C. and 900° C., are shown on FIGS. 4 to 8. In the same time, one can observe that oxygen precipitates in the same condition except for the temperature of 900° C. This phenomenon was not detected at 450° C.

Figure 4:
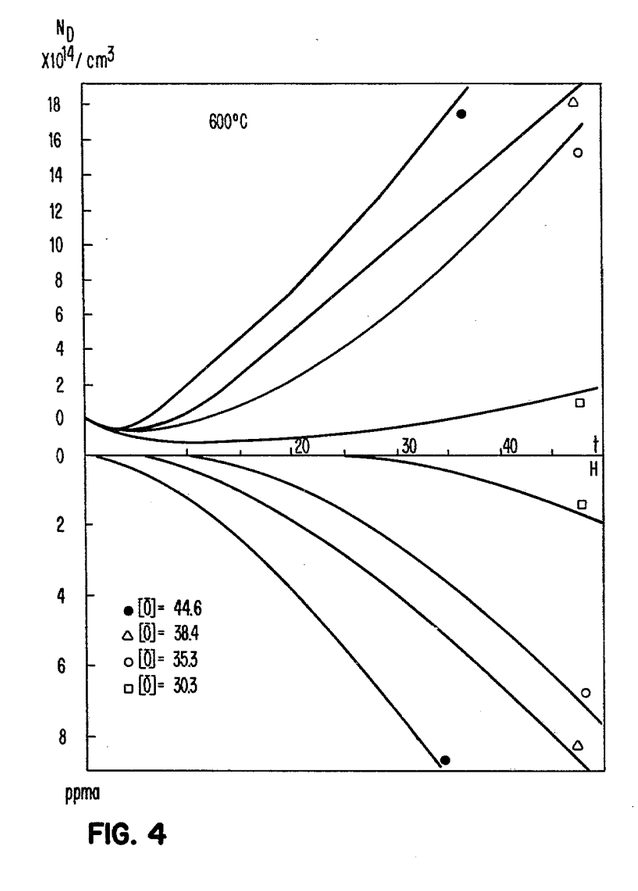
FIGS. 4, 5, 6, 7 and 8 show, on the one hand, the number of the generated donors $N_D$ and, on the other hand, the oxygen precipitation given in ppmA in accordance with the duration (t) of the annealing operation, at annealing temperatures of 600° C., 650° C., 750° C., 825° C. and 900° C., respectively, for various oxygen concentrations.
Figure 5:
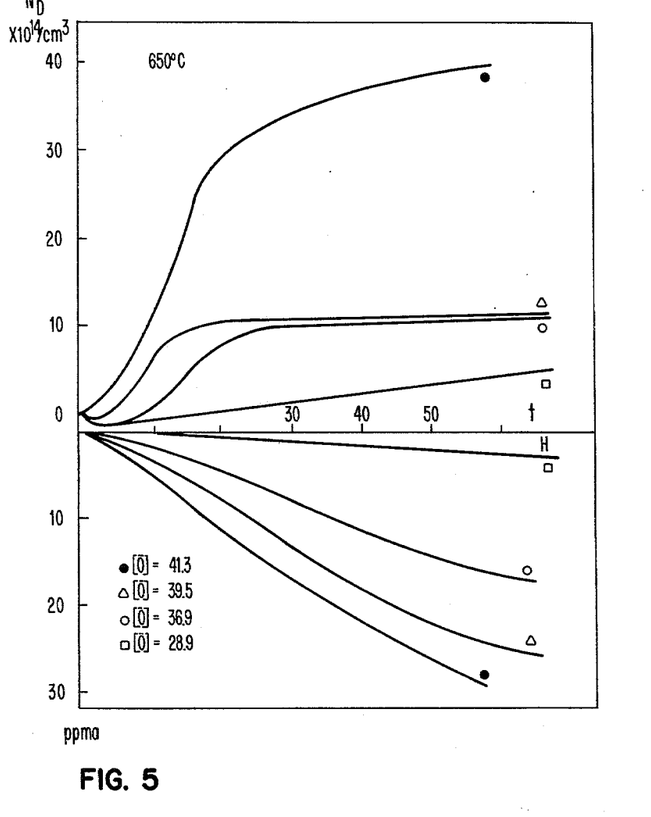
Figure 6:
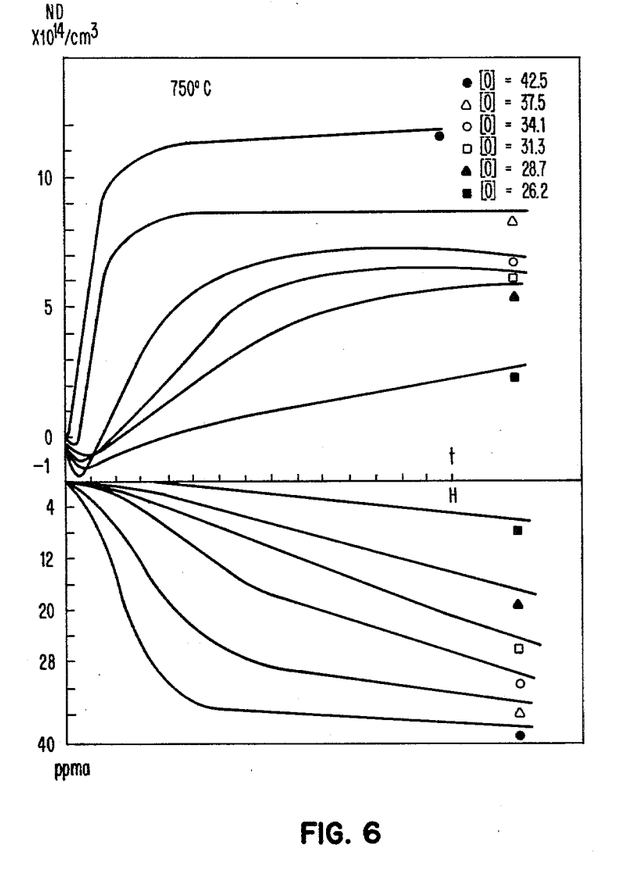

In addition, one can see on FIG. 4 that for times lower than 5 hours, there is no generation of donors. It is the reason why it is recommended to stabilize the rod (or wafer) resistivity at this temperature.

2. Studying the phenomenon.

(a) Resistivity peaks

To quantify the phenomenon for various initial oxygen concentrations, one defines a new parameter MDGH which corresponds to the maximum number of donors generated per hour of annealing (therefore, MDGH corresponds to the maximum slope of curves $N_D = f(t)$ plotted on FIGS. 4 to 8). If MDGH is plotted as a function of annealing temperatures T ranging from 300° to 900° C. for various concentrations $[O]$, one obtains the curve of FIG. 9. The peak described by Kaiser at 450° C. and well known in the art, appears on the figure as well as a new resistivity peak at about 750° C. This peak appears mainly between 650° and 850° C. although it is noticeable between 600° and 900° C.

(b) Relation between the two peaks

Figures 10, 11, 12:
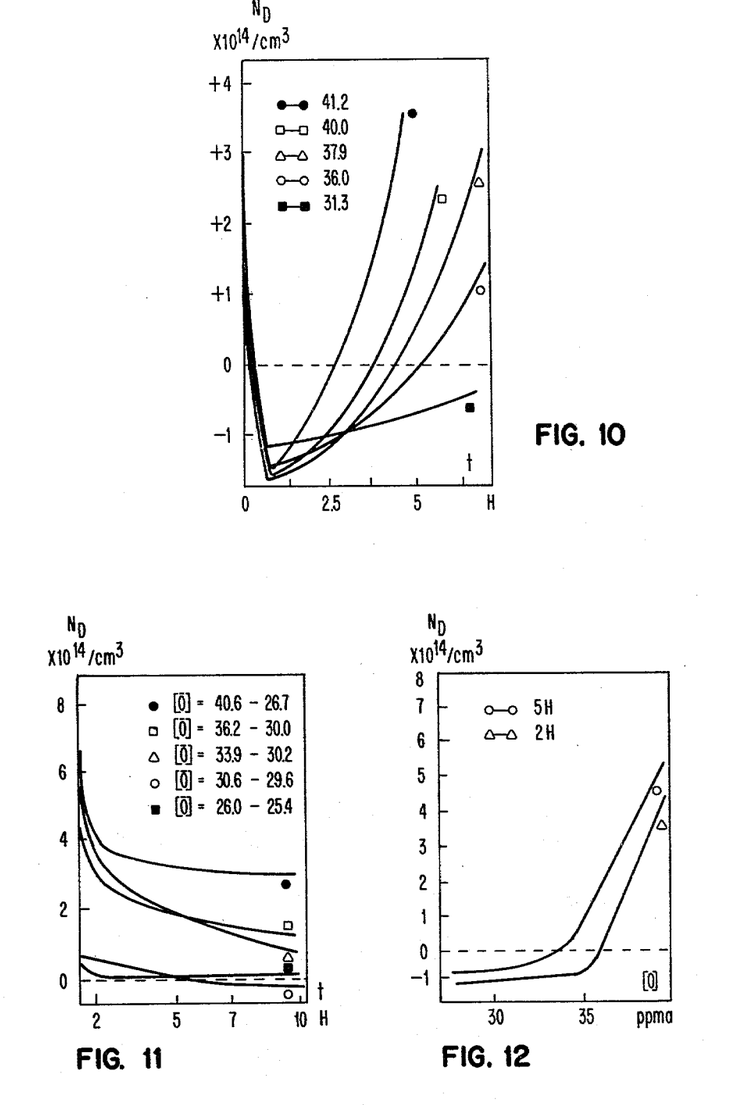
FIG. 10 shows the evolution of the number of donors generated during an annealing operation performed at 450° for 20 hours, according to time t, for a second annealing operation performed at 650° C. and for various initial oxygen concentrations $[\overline{O}]$ given in ppmA.
FIG. 11 shows the annihilation at 1000° C. of the donors generated by an annealing operation performed for 5 hours at 750° C. according to the duration (t) of the annealing operation for wafers with various initial oxygen concentrations $[\overline{O}]$ given in ppmA. The first and second figures, respectively, indicate the initial and final oxygen concentration (given in ppmA), i.e. prior to and after the annealing operation at 750° C.
FIG. 12 shows the evolution of the number of generated donors $N_D$ according to the initial oxygen concentration $[\overline{O}]$ at 825° C. for annealing operations lasting 2 hours and 5 hours.

Although both peaks are related to oxygen, they are different for the following reasons:
O  Existence of a minimum at 600° C.
O  Oxygen precipitates only at the second peak.
However, in order to confirm this point, donors were generated at 450° C. for B 20 hours, then the wafers were treated at 650° C. (FIG. 10). It can be seen that the donors generated at 450° C. are completely destroyed before the generation of the new ones which are therefore, of a different nature.

(c) Stability of the various donors

The donors related to the 450° C. peak are completely destroyed (as shown by Kaiser or on FIG. 10); therefore, they can be neglected at the present time.

It was seen above that the annihilation of the donors generated at 750° C. is much more difficult than the annihilation of the donors generated at 450° C. As shown in FIG. 11, long treatments at high temperatures are required to make said donors disappear. This is effectively very important for controlling the resistivity of FET products which can be submitted to low pressure chemical vapor deposit (LPCVD) performed at about 750° C. Such a method is particularly well described in French Pat. No. 76 35591 fuled by Motorola on Nov. 25, 1976.

In this case, it is possible to retain only the wafers with an oxygen content sufficient to ensure an appreciable gettering.

3. Applications of the results shown on FIG. 9 in the industry.

(a) Stabilizing resistivity

The best temperature for stabilizing resistivity is included between the two peaks, i.e., it is about 600° C., for periods of time less than 3 hours (FIG. 4) to avoid the generation of any donor. In fact, resistivity can be satisfactorily stabilized within the temperature range of 550° to 650° C. for a period of time of 1 to 5 hours.

(b) Controlling the CZ rod oxygen level and defining the method for characterizing said rods Therefore, the problem consists in determining the oxygen concentration or content $[O]$ of the CZ rods with a good accuracy since that, according to this content, donors will be (or not) generated, when applying subsequent thermal treatments, which often involve undesirable variations of resistivity.

Figure 2:
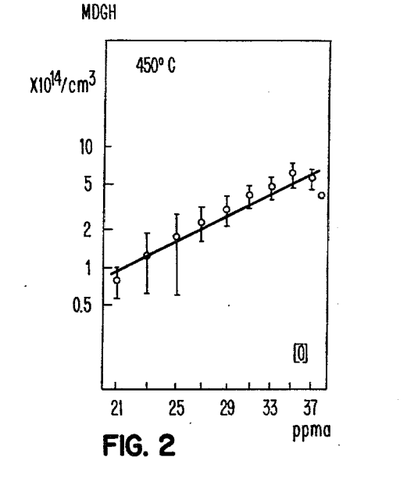
FIG. 2 shows the number of donors generated per hour of annealing (MDGH) according to the initial concentration of oxygen $[\overline{O}]$ given in ppmA at 450° C.

The 450° C. peak can not be used for this purpose. The results shown on FIG. 2 are too inaccurate as described above (paragraph 1.a).

On the other hand, FIGS. 4 to 8 show more or less that the donor generation effect depends very much on the initial oxygen concentration $[\overline{O}]$. On FIG. 7 which corresponds to T = 825° C., it appears that practically no donor is generated when $[\overline{O}] < 35$ while the generation is very significant when $[\overline{O}] \geq 36$. Therefore, the difference is very clear. In addition, this effect appears very quickly. In effect, it is sufficient to perform annealing for 1 to 10 hours and even only for 1 to 6 hours, to distinguish the behaviors. It is also possible to perform annealing for longer periods of time, but this is not of much advantage in the industry.

Figure 9:
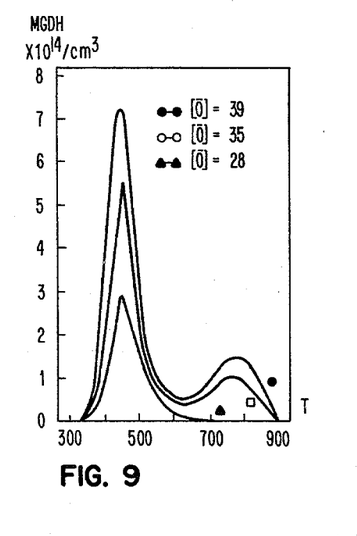
FIG. 9 shows the maximum number of donors generated per hour of annealing (MDGH) according to the annealing temperatures (t) for various initial oxygen concentrations $[\overline{O}]$.

FIG. 9 shows that the donor generation effect around the 750° C. peak is in fact noticeable within the temperature range of 600° to 900° C. which practically corresponds to the useful temperature range. In fact, the effect can be noted at 600° C. (FIG. 4) but a long annealing operation must be performed for almost 20 hours at least to distinguish the different initial concentrations. Therefore, this temperature corresponds to the minimum temperature allowing the characterizing method of this invention to operate. At 900° C. (FIG. 8), the donor generating effect has practically disappeared. This temperature is not of interest and therefore, corresponds to the maximum temperature allowing the method of this invention to operate.

The oxygen contents decrease, in general, from the head (close to the seed) to the tail of the rod. The maximum value will be measured on a portion of the rod consisting in fact in a 1 cm approximately thick wafer cut from the rod head. Conversely, the minimum value will be measured on a portion cut from the rod tail.

Therefore, the characterizing method of this invention consists in:

(1) Cutting a portion from the stabilized rod head (tail) and measuring its resistivity.

(2) Annealing said portion at a temperature ranging from 650° to 850° C. for a period of time ranging from 1 to 6 hours in an atmosphere of neutral nitrogen, for instance.

(3) Chemically etching the surface of this portion to make any silicon which could have been oxidized, to appear and to measure again resistivity.

(4) If the resistivity increment exceeds (or is lower than) a certain number of $\Omega$.cm corresponding to a significant generation of donors, for instance $10^{14}$ donors per $cm^3$, which ultimately corresponds to an undesired initial oxygen concentration, repeating the same process after having removed 3 to 4 cm of rod by cutting another portion of the rod.

EXAMPLES

Figure 7:
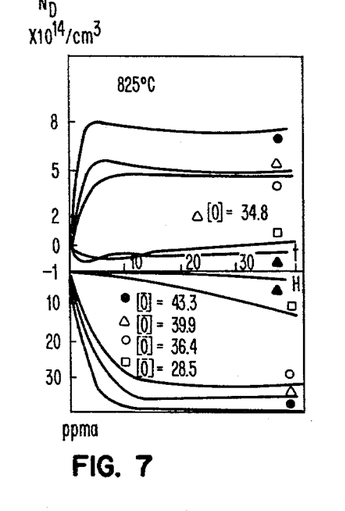
Figure 8:
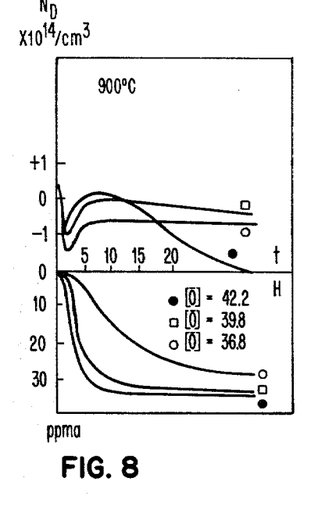

A maximum of 36 ppmA of oxygen is to be ensured in bipolar devices, which avoids any donor generating effect and even prvides a slight annihilating effect, which is desirable for stabilizing the rod resistivity. In this case, the thick wafer (or slug) cut from the rod head, will be annealed at 825° C., for instance, for aproximately two hours and the resistivity increment should be null or very low, which corresponds to a null or very small carrier generating effect (see FIG. 12). It could be possible to define a critical value of the resistivity increment corresponding to a significant donor generation. For instance, the critical value will be 3 $\Omega$.cm for a type P silicon rod of 19 $\Omega$.cm, which corresponds, according to the Irvin curves, to the generation of $10^{14}$ donors per $cm^3$. FIGS. 7 and 12 show the accuracy of the measurement (no increment at 34.8 ppmA and very strong increment above 37 ppmA), which can be compared to the IR accuracy which is 2 ppmA.

In particular, it is shown on FIG. 12 that the annealing operation performed at 825° C. for 2 hours, enables the user to characterize the wafers showing an initial oxygen concentration lower than 36 ppmA while a duration of 5 hours is much appropriate for a value of 33–34 ppmA.

Figure 13:
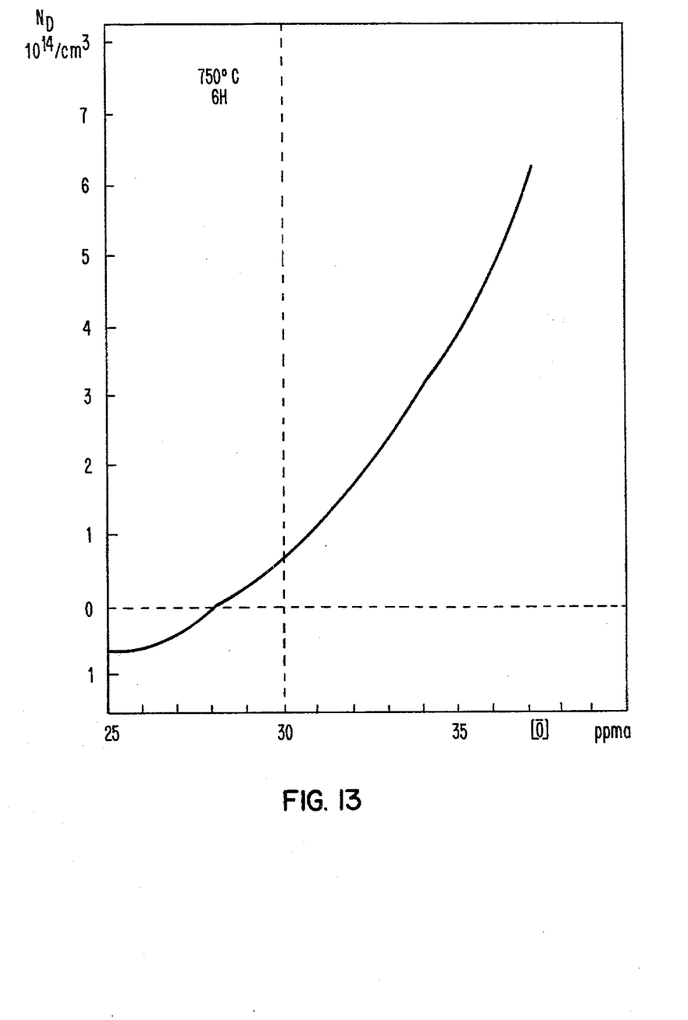
FIG. 13 shows the evolution of the number of generated donors $N_D$ according to the initial oxygen concentration $[\overline{O}]$ for an annealing operation lasting 6 hours at 750° C.

In the case of rods to be used on FET production lines, a minimum level of 30 ppmA approximately, is required to ensure the desired gettering effect. The thick wafer cut from the rod tail will be annealed for instance at 750° C., for 6 hours and the resistivity increment should be checked to make sure that donors have been generated. For instance, the minimum permissible increment will be 3 $\Omega$.cm for an initial resistivity value of type P rod of 19 $\Omega$.cm approximately, which corresponds, as seen above, to the generation of $10^{14}$ donors per $cm^3$, which can be considered as a significant value. If the resistivity increment is lower, the same procedure is repeated after having removed 3 to 4 cm of the rod by cutting another portion of said rod. FIG. 13 also shows the accuracy of this process.

Thus, this characterizing method with an appropriate annealing temperature (in the range of 650° to 850° C.) and an appropriate duration of the annealing operation (from 1 to 6 hours), allows various rods to be characterized. Two important examples concerning the production line were given above but they are not intended to limit the scope of this invention.

(c) Forecasting the strong precipitability of the wafers and the resistivity variations.

When precipitate generation processes are carried out to increase gettering (in accordance with above indicated French Pat. No. 78 26223) and the temperature selected is lower than 850° C., it is possible to detect the wafers with a very strong precipitability by checking the variation of the resistivity (which can be easily understood by referring to the relation existing between the precipitation and the donor effect shown on FIGS. 4 to 7). In addition, for the wafers which have slightly evolved, it is possible to forecast their final value when the donors are eliminated by the treatment applied on the production line.

4. Advantages of the characterizing method of this invention:

(a) On sorting the wafers according to their oxygen contents

The rod portion with an appropriate oxygen content is determined without cutting and polishing thin wafers, which greatly improves the production output. In effect, the method of the prior art consists in cutting all the wafers from a CZ rod stabilized at 650° C. and rectified. Then, these wafers are lapped, polished and at last, their oxygen contents are measured by using I.R. techniques which require a good surface condition. Then an oxygen profile is established in accordance with a groove machined in the wafer flat (refer to the article of D. Mallejac and entitled "Reference Mark for Locating a Wafer in Semiconductor Rods" in the IBM Technical Disclosure Bulletin, Vol. 20, No. 8, January 1978, page 3154). Then the wafers are sorted one by one to retain only the wafers with a good oxygen concentration. Therefore, this method of the prior art is complex and expensive and it is easy to see how the method of this invention is advantageous.

(b) On resistivity stability and oxygen precipitability

Appropriate information is provided about these two fundamental parameters, the specifications of which can be determined very quickly.

While the invention has been particularly shown and described with reference to a preferred embodiment thereof, it will be understood by those skilled in the art that numerous changes in form and detail may be made therein without departing from the spirit and scope of the invention.

What is claimed is:

1. A method for characterizing the oxygen content of a Czochralski grown silicon rod which is to be cut into wafers, comprising the following steps:
   (A) stabilizing the rod by heating;
   (B) cutting a first portion of the rod close to a first end of the rod and measuring its resistivity;
   (C) annealing said portion in a neutral atmosphere at a temperature in the range of approximately 600° to 900° C. for a period of time sufficient to generate donors; and
   (D) cleaning said portion and measuring the resistivity increment to characterize the oxygen concentration from the resistivity increment.

wherein said first end is the rod head and, if the resistivity increment is lower than the critical value corresponding to a significant donor generation, the remaining portion of the rod is selected to be used on bipolar device production lines.

2. The method according to claim 1 in which the temperature range is from 650° to 850° C. and the annealing duration range is from 1 to 6 hours.

3. The method according to claim 1 where if the resistivity increment is higher than this critical value, steps A to D are repeated with a new portion of the remaining portion of the rod approximately adjacent to the first portion and farther from the head of the rod.

4. The method according to claim 1 wherein for selecting the rods with an oxygen concentration lower than 36 ppmA, the annealing temperature is about 825° C. and the annealing duration about 2 hours.

5. The method according to claim 1 in which said first end is the tail of the rod and if the resistivity increment exceeds the critical value which corresponds to a significant donor generation, the remaining portion, of the rod is selected to be used on unipolar device production lines.

6. The method according to claim 5 where if the resistivity increment is lower than this critical value, steps A to D are repeated with another portion of the rod approximately adjacent to the first portion and farther from the rod tail.

7. The method according to claim 5 wherein characterized for selecting the rods with an oxygen concentration exceeding 30 ppmA, the annealing temperature is about 750° C. and the annealing duration about 6 hours.

8. The method according to claim 1, characterized in that the rod is stabilized at 600° C. for 1 to 3 hours.

9. The method according to claim 1 wherein the neutral atmosphere is nitrogen and in the cleaning step includes the removal of the thin layer of surface oxide by rinsing in an acid bath of a mixture of $HNO_3$ and HF.

10. The method according to claim 1 wherein significant donor generation corresponds to the generation of $10^{14}$ donors per $cm^3$.

11. The method according to claim 10 wherein a significant donor generation corresponds to a resistivity increment equal to 3 ohms for a P wafer with a resistivity of 10 ohms-cm.

12. The method according to claim 1 wherein the first portion is about 1 cm thick.

* * * * *